United States Patent [19]
Pericles

[11] Patent Number: 5,224,510
[45] Date of Patent: Jul. 6, 1993

[54] VALVE

[75] Inventor: Nico Pericles, Herznach, Switzerland

[73] Assignee: Ciba-Geigy Corporation, Ardsley, N.Y.

[21] Appl. No.: 606,405

[22] Filed: Oct. 31, 1990

[30] Foreign Application Priority Data

Nov. 8, 1989 [CH] Switzerland .................. 4017/89

[51] Int. Cl.⁵ .................................. G05D 16/00
[52] U.S. Cl. ...................... 137/487.5; 137/341; 251/129.06; 251/333
[58] Field of Search ........... 604/236, 237, 247, 248, 604/249; 137/597, 341, 487.5; 251/129.06, 333

[56] References Cited

U.S. PATENT DOCUMENTS

| | | | |
|---|---|---|---|
| 3,386,472 | 6/1968 | Szonntaph | 137/597 |
| 3,415,427 | 12/1968 | Sharp | 251/333 |
| 3,511,475 | 5/1970 | Pfau | 251/333 |
| 3,605,795 | 9/1971 | Rajakovics | 137/341 |
| 4,316,600 | 2/1982 | Parise et al. | 251/333 |
| 4,494,727 | 1/1985 | Babitzka et al. | 251/129.06 |
| 4,826,135 | 5/1989 | Miella | 251/333 |
| 4,887,636 | 12/1989 | Rothen | 137/487.5 |
| 4,928,920 | 5/1990 | Feild | 251/333 |

Primary Examiner—C. Fred Rosenbaum
Assistant Examiner—Manuel Mendez
Attorney, Agent, or Firm—Marla J. Mathias; Luther A. R. Hall; Harry Falber

[57] ABSTRACT

A high-pressure control valve (2) used in chromatography serves as a counter pressure control valve which, in a separating column, is intended to maintain a specific predeterminable pressure. The valve has a valve seat (12) with an outlet channel opening (18) located in its center and a valve body (13) that cooperates with the valve seat. The valve body (13) can be moved with the aid of a piezo transducer, actively in the opening direction and, while being monitored, actively in the closing direction. The opposed faces of the valve seat (12) and the valve body (13) are so shaped that an annular gap (16) that widens radially towards the outside starting from the opening (18) of the outlet channel is produced. When the valve is in the closed position, this results in the formation of a narrow sealing zone directly at the edge of the opening of the outlet channel.

17 Claims, 4 Drawing Sheets

VALVE

BACKGROUND OF THE INVENTION

The invention relates to a valve, especially a high-pressure control valve.

Such high-pressure valves are used in chromatography (supercritical fluid chromatography-"SFC" for short) at pressures of up to several hundred bar. In chromatography they act as counter pressure control valves which maintain a specific predeterminable pressure in a separating column. They are, however, also used in extraction processes using supercritical media and generally in systems in which it is necessary to monitor and to control the pressure patterns of gases, liquids and supercritical media over time. For operation of the valve it is already known to use an electromagnetic drive that is capable of moving the valve body in the opening direction against a spring force. Valves of that type require the starting position of the valve to be adjusted manually for a specific working range. This adjustment has to be made very carefully and is therefore very time-consuming. In addition, the closing spring force must be such that, on the one hand, sealing closure is possible and, on the other, damage to the valve seat or to a seal in the valve seat is avoided. The closing force of the spring may at most be as great as the magnetic force available for opening.

Owing to the transition in the valve from a region of high pressure to a region of low pressure, when the supercritical medium expands there is a risk that ice will form, which can lead to considerable impairment of the control function of the valve or to destruction of the valve seat. On the other hand, however, it is necessary in the case of preparative work to be able to collect the medium in solid form (ice). The impairment of the functioning of the valve in the case of ice formation is attributable to the fact that ice forms between the valve seat and the valve body, preventing the valve from closing. This applies in the same way to other solid particles that may be contained in the investigation medium.

In electromagnetic control valves in which closing is effected by a spring, the force of the spring is so adjusted to "normal operation" that on the one hand reliable functioning is achieved and on the other hand damage to the valve is avoided. This spring setting is not generally sufficient, however, to overcome ice or other solid particles on closing, so that the valve-control function is disrupted. If the end faces of the valve seat and the valve body oppose one another and rest one on the other in the closed position, the ice or the like can occur as a layer, which means that even greater adjusting forces would be needed to push away those solid particles.

Needle valves, which pose fewer problems when solid bodies and ice are present, are also known, but they are sensitive mechanically.

In order to prevent the formation of ice on the counter pressure control valve and hence to avoid impairment of its functioning, arrangements having multi-stage, generally two-stage, expansion with a plurality of valves are already known, the control valve being arranged in the region of the first expansion stage. The pressure difference in that stage is such that icing cannot occur. This multi-stage arrangement does, however, require additional expenditure.

In order to prevent icing, it is also possible to provide heating means in the region of the control valve. In practice, however, for reasons of space, this is generally possible only with difficulty. In addition, with the given geometry, the heat transfer is generally too low. Furthermore, preparative work cannot be carried out using heated valves.

FR-A-2,425,559 discloses a valve which is opened by means of a piezo-crystal. The valve is closed by means of a mechanical spring. This valve is used for pressures below 1 bar, especially in the introduction of controlled gas streams into a vacuum. This valve is not suitable, however, for use as a high-pressure control valve for pressures of several hundred bar, for example up to 800 bar, since a mechanical spring would not withstand such pressures.

DE-A-3,608,550 describes a three-way valve. That valve has a housing into which at least three valve channels open. Using a piezo-electrically adjustable sealing member, the working channel can be connected either to one valve channel or to the other. This three-way switching valve cannot be used as a counter pressure control valve at pressures of several hundred bar.

A similar three-way switching valve is described in U.S. Pat. No. 3,386,472. In the case of that valve, different channels in the valve are connected with the aid of a magnetically actuatable sealing member. This three-way valve cannot be used as a high-pressure control valve.

SUMMARY OF THE INVENTION

The problem to be solved by the present invention is to provide a high-pressure control valve, especially a two-way high-pressure control valve, which has a high degree of control accuracy over the whole control range and which, moreover, is so constructed that a single expansion stage is adequate, it being possible also to carry out preparative work without adversely affecting the functioning of the control valve. In addition, the throughput volume of the valve should be as low as possible.

To solve this problem it is proposed according to the invention especially that, when the valve is in the closed position, with the valve body resting on the valve seat, there be provided between the valve seat and the valve body an annular gap that widens approximately radially towards the outside from the sealing zone at the edge of the opening of the outlet channel and that a drive which can be actuated in the closing direction be provided for the valve body. This design of the valve components results in a virtually linear sealing contact in the closed position, it being possible, owing to the position of the sealing zone at the edge of the opening of the outlet channel, which is formed by a capillary, for icing to occur only in a very narrow region. Accordingly, the force required to close the valve is substantially reduced, even when icing occurs or when there are other solid particles in the valve. This, in conjunction with the valve's adjusting drive, which operates actively in the closing direction, results even under unfavourable conditions in precise control behaviour of the valve, since the valve position prescribed by the control means is assumed actively in the closing direction also. Consequently, the closing pressure is not fixed and constant for all cases, as with a closing drive in the form of a spring; rather, the control is also active in the closing direction. Under normal conditions, therefore, the drive force on closing the valve will increase only until the predetermined pressure conditions have become established, with the result that the valve is loaded only in accordance with requirements. This contributes to trouble-free operation even over a relatively long period of time.

On the other hand, however, a substantially higher drive force is available as required, especially when the valve is to be closed when ice has formed or there are solid particles in the valve, with the result that no problems occur even with preparative work.

A piezo-electric transducer is advantageously provided as the valve-body closing drive. The use of such a piezo transducer as the adjusting drive for the control valve has the advantage that, with the relatively short adjusting travels provided for in the present use, a large adjusting force is available if needed, for example in the case of ice formation, which force will, however, automatically be reduced correspondingly for normal operation. It is also advantageous for this adjusting drive to monitor both the opening movement and the closing movement, so that the overall structure is simplified. This also promotes a small-volume construction, which makes it possible for the throughput volume of the valve to be kept low. Mixing of the media flowing through can thus be prevented. Heating means can then also more readily be used if need be. The compact construction results in large heat exchange surfaces which improve the heat transfer properties.

The valve body advantageously has an approximately planar closing face opposed to the valve seat, and the valve seat a spherical convex surface with an outlet-channel opening approximately in its center. This preferred embodiment is simple to manufacture, it being possible to produce the spherical rounded surface of the valve seat by, for example, polishing.

Additional developments of the invention are indicated in the further dependent claims. The invention, with its essential details, is explained more extensively below with reference to the drawings.

DETAILED DESCRIPTION OF THE INVENTION

Figure 1:
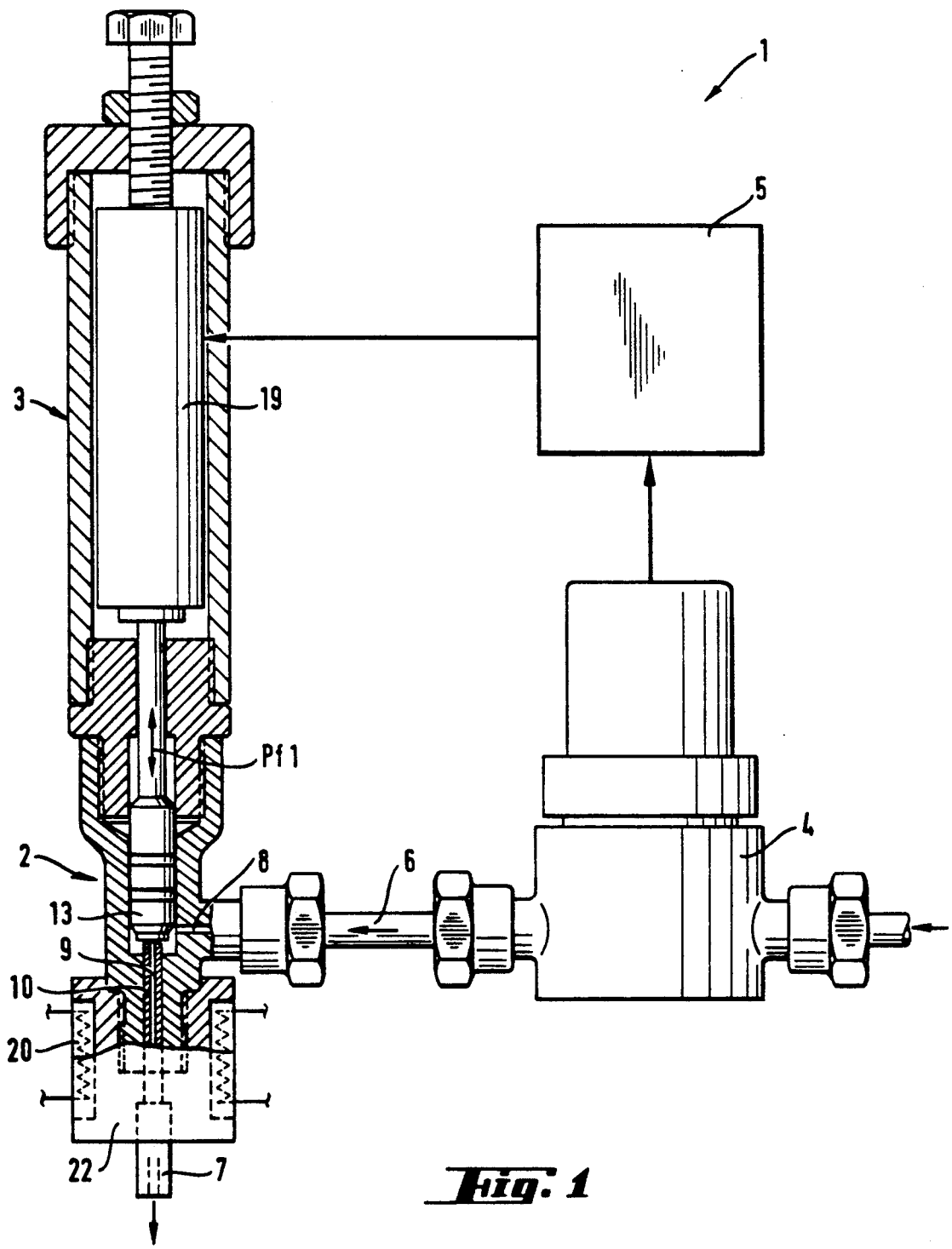
FIG. 1 is a diagrammatic representation of a pressure control device.

The pressure control device 1 shown in FIG. 1 has a high-pressure control valve 2, shown diagrammatically, with an adjusting drive 3. In the chromatography of supercritical flow media, the high-pressure control valve serves as a counter pressure control valve which keeps under specific, predeterminable pressure conditions a separating column that is connected upstream, on the pressure side. At the inlet side of the high-pressure control valve is a pressure-measuring transducer 4 which is connected to an electronic control means 5. The control means is in turn connected to the adjusting drive 3 of the high-pressure control valve, thus producing a closed control loop. The high-pressure control valve 2 has a high-pressure-supply line 6 and a low-pressure side 7 with a transition to atmospheric pressure. Depending on the position of the high-pressure control valve, a corresponding "pile-up pressure" is produced at its high-pressure side, where the packed column (not shown) is also located. The working pressures in that case may be several hundred bar, for example up to 800 bar.

Figure 2:
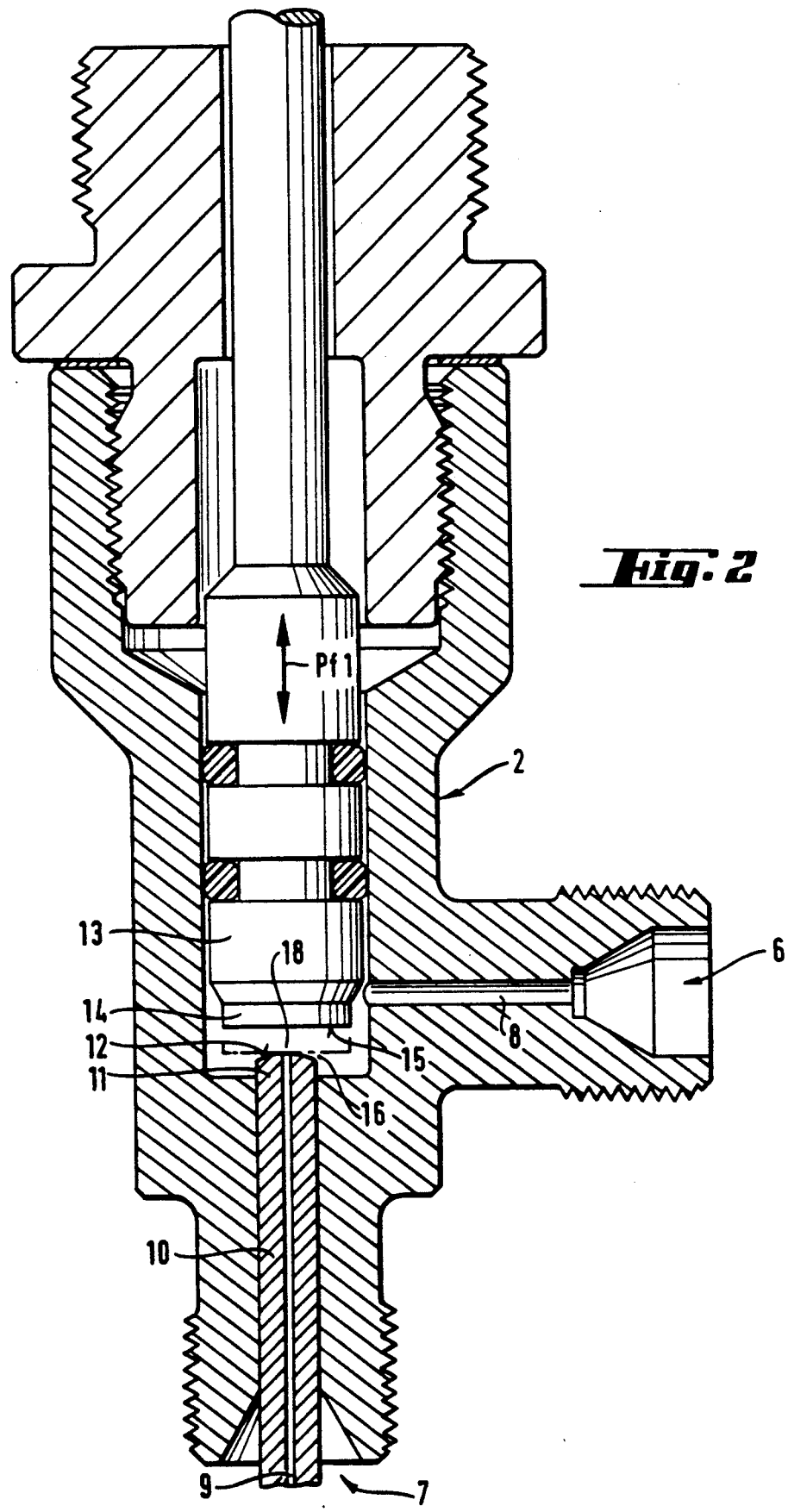
FIG. 2 is a side view of a pressure control valve.

FIG. 2 shows more clearly the structure of the high-pressure control valve 2. It includes a valve housing having an inlet channel 8 connected to the high-pressure-supply line 6, and an outlet channel 9 in the form of a capillary. The outlet channel 9 is located within a small capillary tube 10, the inlet end 11 of which forms a valve seat 12 which cooperates with a valve body 13. The valve body 13 is adjustable in accordance with the double arrow Pf 1 with the aid of the adjusting drive 3 shown in FIG. 1. The valve body 13 has on its face opposed to the valve seat 12 a sealing disc 14 which comes into contact with the valve seat 12 when the valve is closed. The sealing disc 14 may be made of brightly polished metal, but is preferably made of Teflon ® (polytetrafluoroethylene PTFE).

A special feature of the high-pressure control valve 2 according to the invention is the special shaping of the valve body and/or of the valve seat, as is shown in various embodiments according to FIGS. 3 to 7. Formed between the surface of the valve seat 12 and the closing face 15, opposed to the latter, of the valve body 13 is an annular gap 16 which widens approximately radially towards the outside. The shaping of the valve seat 12 and the closing face 15 is such that when the valve is in the closed position, with the valve body resting on the valve seat, there is an annular sealing zone at the edge 17 of the opening of the outlet channel 9 which forms a capillary. This comparatively narrow sealing zone on the one hand improves the sealing in the closed position and on the other hand improves the control properties of the valve, since it results in more favourable throughflow conditions. In addition, solid particles contained in the throughflow medium virtually cease to cause problems, since they are largely prevented from settling by the formation of the annular gap. The narrow sealing zone immediately at the edge of the opening of the capillary also favours the crushing and transporting away through the valve body 13 of any particles remaining there. Solid particles may be, for example, particles of ice formed as a result of the reduction in pressure.

Figure 3:
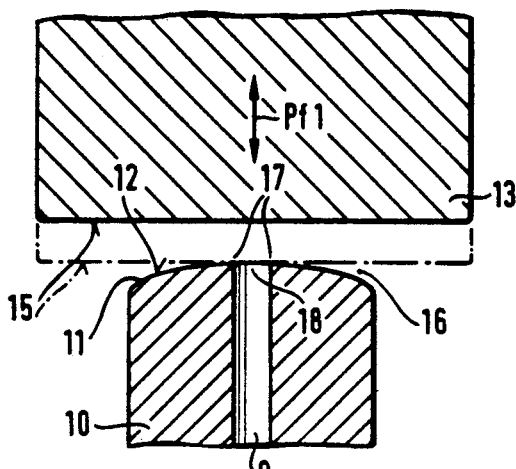
FIGS. 3–7 show different embodiments of valve seats and valve bodies belonging to a pressure control valve.

Common to all the embodiments shown in FIGS. 3 to 7 is the fact that the annular gap 16 widens towards the outside. FIG. 3 shows the preferred embodiment in which the closing face 15 of the valve body is planar and the valve seat opposed to that face has a spherical, convex surface. In the middle of that spherical surface of the valve seat 12 is the opening 18 of the outlet channel 9. In addition, this preferred embodiment is, especially, simple to produce.

Figure 4:
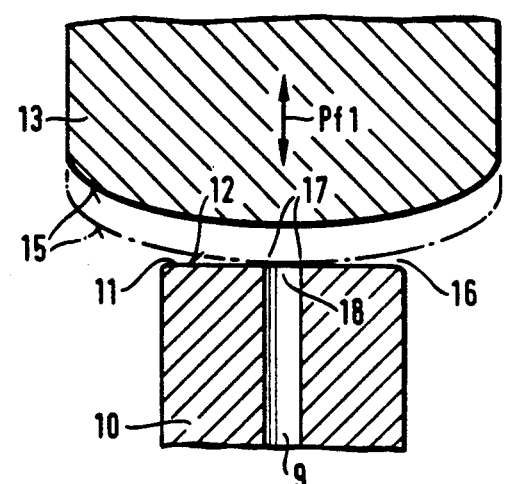

FIG. 4 shows a planar valve seat and a valve body 13 that is domed in a convex manner on its closing face 15.

Figure 5:
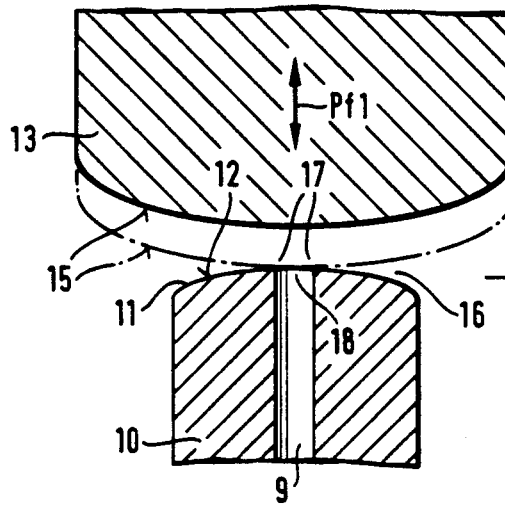

FIG. 5 shows an embodiment in which both the closing face 15 of the valve body 13 and the surface of the valve seat 12 are domed in a convex manner.

Figure 6:
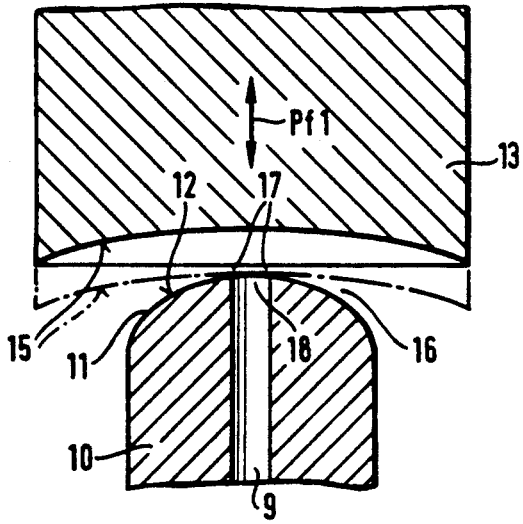

FIG. 6 shows an embodiment in which the closing face 15 of the valve body 13 is domed in a concave manner, while the surface of the valve seat is domed in a convex manner. The radius of curvature of the concave face is in this case considerably greater than that of the convex face of the valve seat, resulting again in an annular gap 16 that widens towards the outside.

Figure 7:
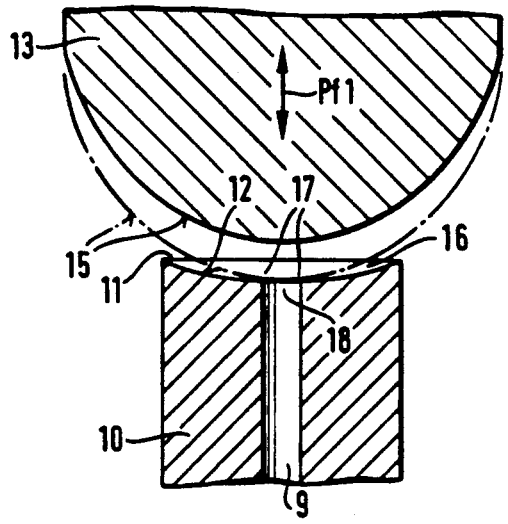

FIG. 7 shows practically the reverse of the embodiment shown in FIG. 6—the face of the valve seat is concave and the closing face 15 of the valve body 13 is curved in a convex manner, the radius of curvature of the concave dome being greater in this case than the radius of curvature of the convex dome of the closing face 15. In this case again an annular gap 16 that widens radially towards the outside is formed.

Figure 8:
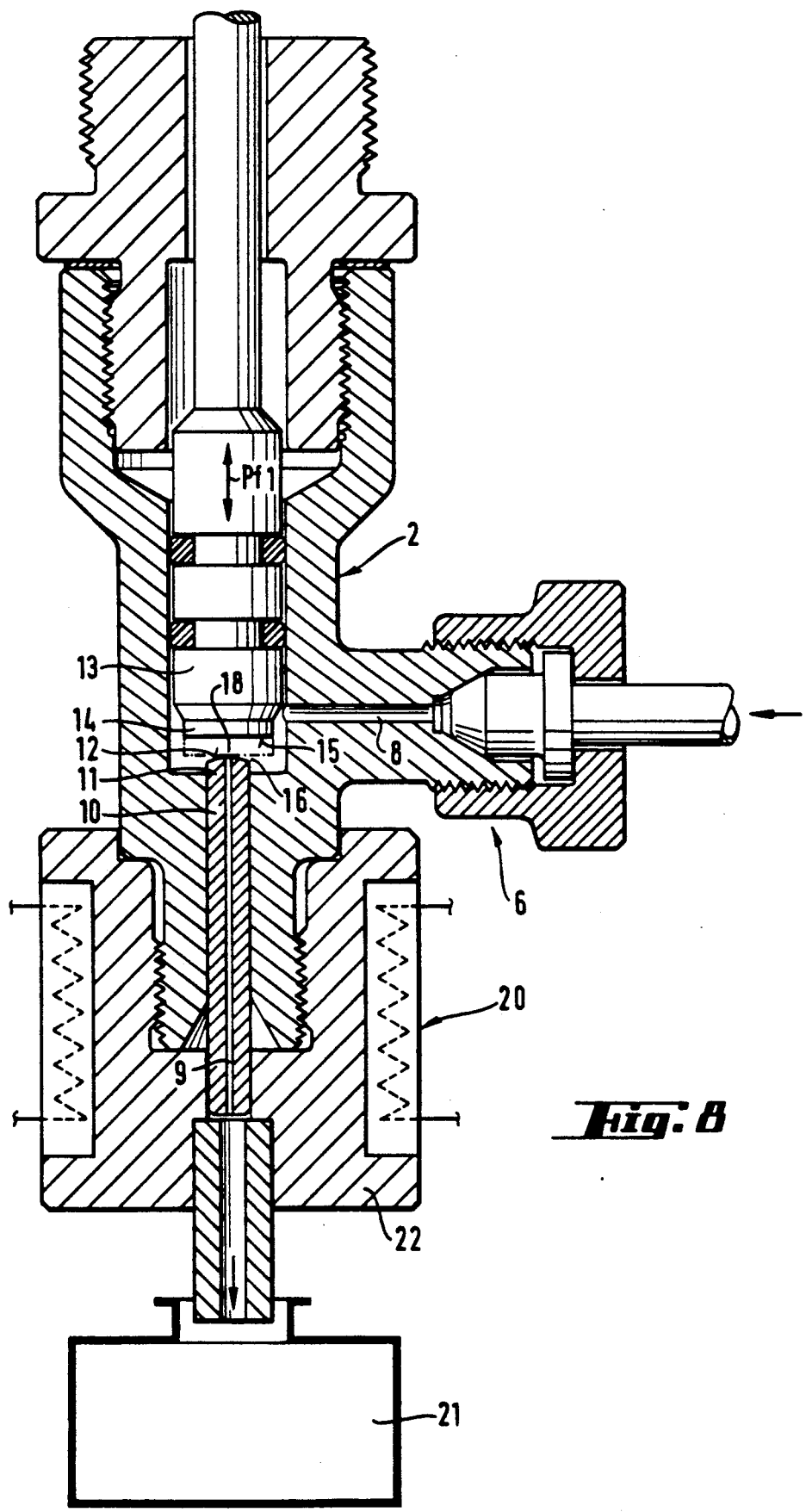
FIG. 8 is a side view of a pressure control valve similar to the embodiment according to FIG. 2, but in this case with an additional device.

A piezo transducer 19 shown in FIG. 1 is used as the adjusting drive 3 for the valve body 13. The piezo transducer is capable of moving the valve body 13 actively in the closing direction and of moving the valve body 13 by a precisely defined length of travel in the opening direction. With short lengths of travels, large moving forces can be produced. This, in conjunction with the special shaping of the opposed faces of the valve seat 12 and the valve body 13, results in especially favorable operating conditions, it being possible especially to work with very high pressures (for example up to 800 bar) and even solid particles in the valve region failing to cause functional disturbances. Owing to the adjusting drive that is active in the closing direction and the comparatively narrow sealing zone, any solid particles that may be present can be pushed away without impairing the good control properties of the valve. Especially in the case of preparative work, in which the medium is ejected at the low-pressure side 7 of the valve in the form of dry ice, the situation described above is of considerable advantage. If ice forms in the valve region in the course of preparative work, this does not lead to disturbances of functioning as it has done hitherto, since on the one hand the active closing drive of the valve and on the other the shaping of the closing face of the valve body, or of the valve seat, allow the ice to be overcome, with the result that no problems occur. A single expansion stage is therefore sufficient. FIGS. 1 and 8 show a broader embodiment than that in FIG. 2, having a heating means 20 arranged in the region of the valve, especially in the region of the valve seat 12. If this heating means 20 remains switched off, preparative work in which dry ice is ejected on the low-pressure side 7 is possible, the dry ice (snow) containing the products to be isolated, and can then be caught in a container 21 indicated in FIG. 8 and collected. For analytical measurement chromatography, the heating means 20 is switched on and the heating block 22 located around the outlet channel 9 is brought, for example, to a temperature, which is preferably thermostatically controlled, of 45° C. In this case there is no ice formation on expansion of the carbon dioxide, which is most commonly used in such processes.

Overall, the measures according to the invention-use of a piezo adjusting drive and special shaping of the valve seat and valve body-virtually eliminate the risk of blockage, closure or even destruction of the capillary opening 18 by the formation of ice or other solid particles. This results, inter alia, in a simplified overall structure and also in increased operational reliability.

All the features indicated in the description, the claims and the drawings may be inventive both individually and in any desired combination with one another.

What is claimed is:

1. A valve for use in controlling pressure of a supercritical medium, comprising:
    a valve housing having an outlet channel with an inlet opening and having an inlet channel;
    a valve seat provided in said valve housing at said inlet opening of said outlet channel;
    a valve body movably mounted in said valve housing, said valve body and said valve seat having mutually opposing contact surfaces;
    an adjusting drive means for adjusting the position of said valve body relative to said valve seat in order to control and maintain the pressure of the supercritical medium in said inlet channel upstream of said valve body and for adjusting a closing pressure of said valve body against said valve seat;
    wherein said opposing contact surfaces of said valve body and said valve seat are made of incompressible materials and are respectively shaped such that, when said valve body is in a closed position in which it abuts said valve seat, said contact surface of said valve body is in virtual line contact with said contact surface of said valve seat and an annular gap is formed between said mutually opposing contact surfaces of said valve body and said valve seat, respectively, said annular gap widening approximately radially outwardly from the virtual line contact between said mutually opposing contact surfaces of said valve body and said valve seat, respectively, such that said valve body, said valve seat and said adjusting drive means together define a means for crushing any ice formed on said valve seat and said valve body; and
    wherein said adjusting drive means is adapted to force said valve body against said valve seat with a pressure sufficient to overcome any ice which may have formed on said mutually opposing contact surfaces of said valve body and said valve seat, respectively, and wherein said pressure is adjustable by operation of said adjusting drive means.

2. A valve as recited in claim 1, wherein said adjusting drive means comprises a piezoelectric transducer.

3. A valve as recited in claim 2, wherein said adjusting drive means further comprises a pressure sensor arranged upstream of said valve body, and a control means responsive to said pressure sensor for controlling operation of said piezoelectric transducer.

4. A valve as recited in claim 3, wherein said contact surface of said valve seat is spherical, and said inlet opening of said outlet channel is located approximately centrally of said contact surface of said valve seat.

5. A valve as recited in claim 4, wherein said contact surface of said valve seat is approximately planar.

6. A valve as recited in claim 4, wherein said contact surface of said valve body is spherical.

7. A valve as recited in claim 4, wherein said contact surfaces of both of said valve seat and said valve body are convex.

8. A valve as recited in claim 3, wherein said contact surface of said valve seat is approximately planar, and said contact surface of said valve body is spherical.

9. A valve as recited in claim 3, wherein said contact surface of one of said valve seat and said valve body is convex, and said contact surface of the other of said valve seat and said valve body is concave; and
    the radius of curvature or angle of inclination is greater for the one of said contact surfaces which is concave than for the one of said contact surfaces which is convex.

10. A valve as recited in claim 3, wherein
said contact surface of said valve seat is convex, and
said inlet opening of said outlet channel is located approximately centrally of said contact surface of said valve seat.

11. A valve as recited in claim 3, wherein
said contact surface of said valve seat is conical, and
said inlet opening of said outlet channel is located approximately centrally of said contact surface of said valve seat.

12. A valve as recited in claim 3, wherein
said contact surface of said valve seat is approximately planar, and said contact surface of said valve body is convex.

13. A valve as recited in claim 3, wherein
said contact surface of said valve seat is approximately planar, and said contact surface of said valve body is conical.

14. A valve as recited in claim 1, further comprising
a seal mounted on said contact surface of said valve body.

15. A valve as recited in claim 1, further comprising
a heater mounted to said valve housing near said valve seat.

16. A valve as recited in claim 1, further comprising
a sealing disc mounted on said contact surface of said valve body, said sealing disc being formed of a brightly polished metal.

17. A valve as recited in claim 1, wherein
said adjusting device means, said valve body and said valve seat together define a means for controlling a pile-up pressure of up to 800 bar upstream of said valve body and said valve seat.

* * * * *